United States Patent [19]

Grollier et al.

[11] Patent Number: 4,971,786
[45] Date of Patent: Nov. 20, 1990

[54] COMPOSITION AND PROCESS FOR THE TREATMENT OF CARE OF THE HAIR

[75] Inventors: Jean F. Grollier; Daniele Cauwet, both of Paris, France

[73] Assignee: L'Oreal, Paris, France

[21] Appl. No.: 285,603

[22] Filed: Dec. 16, 1988

[30] Foreign Application Priority Data

Dec. 18, 1987 [LU] Luxembourg .............................. 87081

[51] Int. Cl.$^5$ ............................................. A61K 7/075
[52] U.S. Cl. ...................................... 424/047; 424/070
[58] Field of Search .................................. 424/70, 47

[56] References Cited

U.S. PATENT DOCUMENTS

| | | | |
|---|---|---|---|
| 4,144,326 | 3/1979 | Luedicke, Jr. et al. | 424/70 |
| 4,387,090 | 6/1983 | Bohch, Jr. | 429/70 |
| 4,663,159 | 5/1987 | Brode, III et al. | 424/70 |
| 4,801,447 | 1/1989 | Gum | 424/70 X |

FOREIGN PATENT DOCUMENTS

| | | |
|---|---|---|
| 0155806 | 9/1985 | European Pat. Off. . |
| 56414 | 4/1982 | Japan .................................... 424/70 |
| 850364 | 8/1985 | PCT Int'l Appl. . |
| 2165550 | 4/1986 | United Kingdom . |
| 2188060 | 9/1987 | United Kingdom . |

OTHER PUBLICATIONS

Chemical Abstracts, 101 (1985), Aug., No. 8, Columbus, Ohio, pp. 295-296.
2216 Household & Personal Products Industry 21 (1984), Jan., No. 1, p. 70.
2176 Seifen-Ole-Fette-Wachse, vol. 109 (1983), Oct., No. 17, pp. 499-500.

*Primary Examiner*—Merrell C. Cashion, Jr.
*Assistant Examiner*—Susan S. Rucker
*Attorney, Agent, or Firm*—Marshall, O'Toole, Gerstein, Murray & Bicknell

[57] ABSTRACT

The invention relates to a cosmetic composition for the treatment and care of the hair, containing, in a cosmetically acceptable medium:
at least one cationic surfactant agent of formula (I):

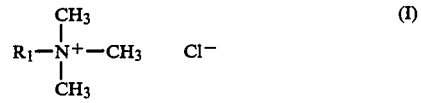

in which $R_1$ denotes a mixture of alkenyl and/or alkyl radicals having from 14 to 22 carbon atoms, derived from tallow fatty acids;
at least one quaternized hydroxyalkylcellulose polymer; and
at least one ethoxylated copolymer of dimethylsiloxane/3-hydroxypropylmethylsiloxane.

15 Claims, No Drawings

COMPOSITION AND PROCESS FOR THE TREATMENT OF CARE OF THE HAIR

The present invention relates to new cosmetic compositions for the treatment and care of the hair.

It is well known that the hair is generally sensitized to various extents by the action of atmospheric agents, as well as by the action of treatments such as bleaching, permanent-waving and/or dyeing, so that the hair is often difficult to disentangle and to style.

One of the means generally employed for improving the disentangling and softness of the hair, sensitized or otherwise, consists in using surfactant agents which are cationic in nature.

Such agents have, however, the drawback of weighing down the hair and giving it a greasy appearance.

These same drawbacks are emphasized in the case of fine hair which lacks hold, liveliness and volume.

Rinsing compositions, such as those described in U.S. Pat. No. 4,144,326, based on cationic surfactant agents such as a mixture of dodecyltrimethylammonium and dialkyldimethylammonium chloride, the compositions being thickened with a quaternized cellulose, have already been recommended.

Some rinsing compositions of the prior art contain a quaternary ammonium salt in combination with a cationic cellulose to form a protective film on the hair, as described in Japanese Pat. No. 79/135,234.

All these compositions have, however, the disadvantage of weighing down the hair. In addition, hair treated with such rinsing compositions lacks body and liveliness after drying.

Applicants has now discovered, surprisingly, that by combining a trimethylalkylammonium chloride, a quaternized hydroxyalkylcellulose polymer and a polyorganosiloxane/polyoxyalkylene copolymer, exceptional properties of body, hold and liveliness which were not possessed by earlier compositions were obtained on the hair.

The subject of the invention hence consists of a cosmetic composition for the treatment and care of the hair, containing, in a cosmetically acceptable aqueous medium, a trimethylalkylammonium chloride, a quaternized hydroxyalkylcellulose polymer and a polyorganosiloxane/polyoxyalkylene copolymer.

The subject of the invention is also a process for treatment and care of the hair employing such a composition.

Other subjects of the invention will become apparent on reading the description and the examples which follow.

The cosmetic composition intended for the treatment and care of the hair, according to the invention, is essentially characterized in that it contains, in a cosmetically acceptable aqueous medium:
at least one cationic surfactant agent of formula (I):

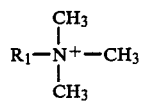

in which $R_1$ denotes a mixture of alkenyl and/or alkyl radicals having from 14 to 22 carbon atoms, derived from tallow fatty acids;
at least one quaternized hydroxyalkylcellulose polymer; and
at least one polyorganosiloxane/polyoxyalkylene copolymer.

Preferred cationic surfactant agents of formula (I) are those sold by the company AKZO under the name ARQUAD, or by the company CECA PROCHINOR under the name NORAMIUM MS 50.

The quaternized hydroxyalkylcellulose polymer used according to the invention is preferably chosen from:
(1) a cellulose ether polymer derived from quaternary ammonium, having a molecular weight of 100,000 to 3,000,000, corresponding to the structural formula:

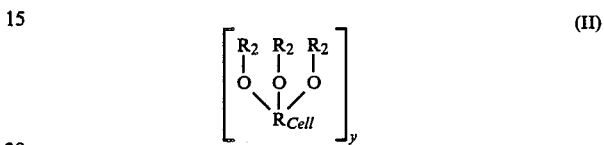

where $R_{Cell}$ is the residue of an anhydroglucose unit, y is a number equal to approximately 50 to approximately 20,000, and each $R_2$ individually denotes a substituent which is a group of general formula:

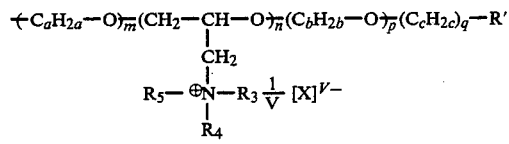

where
a is an integer equal to 2 or 3;
b is an integer equal to 2 or 3;
c is an integer equal to 1 to 3;
m is an integer equal to 0 to 10;
n is an integer equal to 0 to 3;
p is an integer equal to 0 to 10;
q is an integer equal to 0 or 1;
R' is a hydrogen atom or a radical of formula:

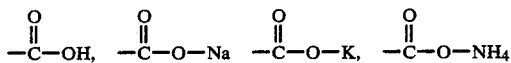

it being clearly understood that when q is equal to zero,
R' denotes —H;
$R_3$, $R_4$ and $R_5$, taken individually, each denote an alkyl, aryl, aralkyl, alkylaryl, cycloalkyl, alkoxyalkyl or alkoxyaryl radical, it being possible for each of the radicals $R_3$, $R_4$ and $R_5$ to contain up to 10 carbon atoms, it being clearly understood that, in the case of an alkoxyalkyl radical, there are at least 2 carbon atoms separating the oxygen atom from the nitrogen atom, and it also being clearly understood that the total number of carbon atoms present in the radicals denoted by $R_3$, $R_4$ and $R_5$ is between 3 and 12;
$R_3$, $R_4$ and $R_5$, taken together, can denote, with the nitrogen atom to which they are attached, one of the following radicals: pyridine, α-methylpyridine, 3,5-dimethylpyridine, 2,5-dimethylpyridine, 2,4,6-trimethylpyridine, N-methylpiperidine, N-ethylpiperidine, N-ethylpiperidine, N-methylmorpholine or N-ethylmorpholine;
X is an anion; V is an integer equal to the valency of X; the average value of n per anhydroglucose unit in this cellulose ether is between 0.01 and approximately 1, and the average value of m+n+p+q) per anhydroglucose unit in this cellulose ether is between approximately 0.01 and approximately 4.

The most especially preferred polymers are those corresponding to the formula (II) above in which a and b are equal to 2, q is equal to 0, m, n and p having the abovementioned values, R' denotes hydrogen and $R_3$, $R_4$ and $R_5$ denote methyl. The average values per anhydroglucose unit are 0.35 to 0.45 for n and 1 to 2 for the sum m+p; X denotes chloride.

The preferred ethers according to the invention have viscosities at 25° C. of 50 to 35,000 centipoises in aqueous solution at a concentration of 2% by weight, measured by ASTM method D-2364-65 (Brookfield model LVF viscometer, 30 rpm, spindle No. 2), and those which are especially preferred are those sold by the firm Union Carbide Corporation under the brand names "JR-125", "JR-400" and "JR-30M", which denote, respectively, a polymer of the type described above having a viscosity equal to 125 centipoises, 400 centipoises and 30,000 centipoises.

(2) a cellulose derivative or a copolymer of cellulose grafted with a water-soluble quaternary ammonium monomer.

The water-soluble quaternary ammonium monomers are chosen, in particular, from methacryloylethyltrimethylammonium, methacrylamidopropyltrimethylammonium and dimethyldiallylammonium salts, and in particular the halides such as the chlorides or methosulphates.

The cellulose derivatives are preferably chosen from hydroxyalkylcelluloses such as hydroxymethyl- or hydroxyethyl- or hydroxypropylcelluloses.

The especially preferred products consist of the copolymer of hydroxyethylcellulose grafted by a free-radical method with diallyldimethylammonium chloride, sold by the company NATIONAL STARCH under the name "CELQUAT L 200" or "CELQUAT H 100".

The polyorganosiloxane/polyoxyalkylene copolymer used according to the invention is preferably an alkoxylated polydi($C_1$–$C_4$ alkyl)siloxane in which some of the di($C_1$–$C_4$ alkyl)siloxane units are modified by substitution of one of the alkyl groups with hydroxy($C_1$–$C_4$ alkyl) groups, and more especially an ethoxylated polydimethylsiloxane in which some of the dimethylsiloxane units are modified by the substitution of one of the methyl groups with 3-hydroxypropylmethyl groups, such as the products sold by the company UNION CARBIDE under the name SILWET TM The molecular weight of these copolymers is between 500 and 10,000, and preferably between 550 and 6,000.

A more especially preferred representative of this type of silicone, according to the invention, is that sold by UNION CARBIDE under the name SILWET 7600, the molecular weight of which is approximately 5,000.

The cationic surfactant agent of formula (I) is preferably used in proportions of 0.5 to 2.5% by weight relative to the total weight of the composition.

The quaternized hydroxyalkylcellulose polymer is preferably used in proportions of 0.5 to 2.5% by weight relative to the total weight of the composition.

The polyorganosiloxane/polyoxyalkylene copolymer is preferably used in proportions of 0.4 to 3% by weight relative to the total weight of the composition.

A more especially preferred cosmetic composition for hair treatment, according to the invention, contains, in a cosmetically acceptable aqueous medium:
0.7 to 2% by weight of cationic surfactant agent of formula (I);
1 to 2% by weight of cellulose ether polymer derived from quaternary ammonium, especially the product sold by the company UNION CARBIDE under the name JR-400; and
0.6 to 1% by weight of ethoxylated dimethylsiloxane/3-hydroxypropylmethylsiloxane copolymer, especially the product sold by the company UNION CARBIDE under the name SILWET 7600.

The cosmetic compositions for the treatment and care of the hair are presented in the form of an aqueous solution, thickened or otherwise, a cream, an emulsion, a gel, an aerosol foam or a spray.

The aqueous solutions contain either water or a water/solvent mixture. The solvents are preferably chosen from monohydric alcohols, polyhydric alcohols, glycol ethers and fatty acid esters. There may be mentioned, more especially, lower alcohols such as ethanol, n-propanol, isopropanol and n-butanol, polyhydric alcohols such as ethylene glycol, diethylene glycol and propylene glycol, and glycol ethers such as mono- or diethylene glycol alkyl ethers.

These compositions can contain, in addition to the compounds mentioned in the invention, other cationic surfactant agents and agents customarily used in cosmetics, such as perfumes, colourings, preservatives, sequestering agents, thickeners, emulsifiers, emollients and other adjuvants customarily used in hair-care compositions. They do not contain active substances having detergent, wetting and foaming properties, enabling the hair to be cleansed.

The cosmetic compositions according to the invention which are presented in thickened or gel form contain thickeners in the presence or absence of solvents. The thickeners are preferably chosen from sodium alginate, gum arabic, cellulose derivatives such as methylcellulose, hydroxymethylcellulose, hydroxyethylcellulose, hydroxypropylcellulose, hydroxyporpylmethylcellulose and carboxymethylcellulose, guar gum or its derivatives, xanthan gum or scleroglucans. It is also possible to obtain a thickening of the compositions by mixing polyethylene glycol and polyethylene glycol stearate or distearate, or by a mixture of amide and phosphoric ester.

The concentration of thickener can vary from 0.1 to 30% by weight, and preferably between 0.2 and 15% by weight, relative to the total weight of the composition.

The different cosmetic compositions for the treatment and care of the hair may be presented under pressure, in the form of an aerosol can, and used in the form of an aerosol foam. They are packaged in this case in the presence of one or more propellant gases.

The propellant gases used for pressurizing the cosmetic formulations are present in proportions not exceeding 25%, and preferably 15%, relative to the total weight of the composition. By way of propellant gases, it is possible to use carbon dioxide, nitrogen, nitrous oxide, volatile hydrocarbons such as butane, isobutane, propane and mixtures thereof, and non-hydrolysable chlorinated and/or fluorinated hydrocarbons such as, for example, those sold under the name FREON by the company DU PONT DE NEMOURS and belonging, in particular, to the categories of fluorochlorohydrocarbons such as dichlorodifluoromethane or Freon 12 and dichlorotetrafluoroethane or Freon 114. These propellants may be used alone or in combination; there may be mentioned in particular, a mixture of Freon 114/12 in proportions varying between 40:60 and 80:20.

The pH of these compositions may be adjusted with an alkalinizing or acidifying agent customarily used in the cosmetic field. The pH is generally between 3 and 10, depending on the application envisaged. It is adjusted using alkalinizing or acidifying agents that are well known in the state of the art.

The cosmetic compositions are intended for the treatment and care of the hair. A cosmetic treatment denotes a treatment intended for improving the appearance, feel and shape of the hair.

The process for treatment of the hair, according to the invention, consists in applying the cosmetic compositions as defined above on the hair, and in following this, where appropriate after an exposure time of 1 to 30 minutes, with a rinse.

The cosmetic compositions according to the invention are preferably used as a product to be rinsed before or after shampooing, before of after dyeing or bleaching, before or after permanent-waving or straightening.

The examples which follow are designed to illustrate the invention, no limitation of the latter being implied.

EXAMPLE 1

A transparent gel for dyed hair having the following composition is prepared:

| | |
|---|---|
| Polymer of hydroxyethylcellulose and epichlorohydrin, quaternized with trimethylamine, sold by the company UNION CARBIDE under the name JR 400 | 1.8 g AS |
| Hydroxyethylcellulose sold by the company HERCULES under the name NATROSOL 250 HHR | 1.2 g AS |
| Trimethylalkylammonium chloride (alkyl = mixture of alkenyl and/or alkyl radicals, having 14 to 22 carbon atoms, derived from tallow fatty acids), sold by the company AKZO at a concentration of 30% AS in aqueous solution, under the name ARQUAT T 30 | 1.8 g AS |
| Ethoxylated copolymer of dimethylsiloxane/3-hydroxypropylmethylsiloxane, sold by the company UNION CARBIDE under the name SILWET 7600 | 0.72 g AS |
| Mixture of propylene glycol and 5-bromo-5-nitro-1,3-dioxane, sold by the company HENKEL under the name BRONIDOX L | 0.3 g AS |
| Perfume, colouring, preservative qs | |
| HCl qs pH 6 | |
| Water | qs 100.0 g |

EXAMPLE 2

An after-shampoo to be rinsed, having the following composition, is prepared:

| | |
|---|---|
| Polymer of hydroxyethylcellulose and epichlorohydrin, quaternized with trimethylamine, sold by the company UNION CARBIDE under the name JR 400 | 1.8 g AS |
| Trimethylalkylammonium chloride (alkyl = mixture of alkenyl and/or alkyl radicals, having 14 to 22 carbon atoms, derived from tallow fatty acids), sold by the company AKZO under the name ARQUAT T 30 in aqueous solution at a concentration of 30% AS) | 1.5 g AS |
| Distearyldimethylammonium chloride | 0.3 g AS |
| Mixture of cetylstearyl alcohol and cetylstearyl alcohol oxyethylenated with 33 moles of ethylene oxide, sold by the company HENKEL under the name SINNOWAX AO | 2.0 g |
| Ethoxylated copolymer of dimethylsiloxane/3-hydroxypropylmethylsiloxane, sold by the company UNION CARBIDE under the name SILWET 7600 | 0.72 g AS |
| Hydroxyethylcellulose sold by the company HERCULES under the name NATROSOL 250 HHR | 0.5 g |
| Perfume, preservative, colouring qs | |
| NaOH qs pH 6 | |
| Water | qs 100.0 g |

EXAMPLE 3

An after-shampoo lotion having the following composition is prepared:

| | |
|---|---|
| CELQUAT L 200 sold by the company NATIONAL STARCH | 1.2 g |
| Trimethylalkylammonium chloride (alkyl = mixture of alkenyl and/or alkyl radicals, having 14 to 22 carbon atoms, derived from tallow fatty acids), sold by the company AKZO at a concentration of 30% AS in aqueous solution, under the name ARQUAT T 30 | 2.0 g AS |
| Ethoxylated copolymer of dimethylsiloxane/3-hydroxypropylmethylsiloxane, sold by the company UNION CARBIDE under the name SILWET 7600 | 1.0 g |
| Perfume, colouring, preservative qs | |
| HCl qs pH 6.5 | |
| Water | qs 100.0 g |

This lotion is applied on washed and towel-dried hair. After rinsing with water, the wet hair disentangles readily, the dry hair is bouffant, soft and light and the styling possesses good hold.

EXAMPLE 4

An after-permanent-waving rinsing composition is prepared:

| | |
|---|---|
| CELQUAT H 100 sold by the company NATIONAL STARCH | 1.0 g |
| Trimethylalkylammonium chloride (alkyl = mixture of alkenyl and/or alkyl radicals, having from 14 to 22 carbon atoms, derived from tallow fatty acids), sold by the company AKZO at a concentration of 30% AS in aqueous solution, under the name ARQUAT T 30 | 0.8 g AS |
| Ethoxylated copolymer of dimethylsiloxane/3-hydroxypropylmethylsiloxane, sold by the company UNION CARBIDE under the name SILWET 7600 | 0.6 g |
| Mixture of cetylstearyl alcohol and cetylstearyl alcohol oxyethylenated with 33 moles of ethylene oxide, sold by the company HENKEL under the name SINNOWAX AO | 3.0 g |
| Cetylstearyl alcohol oxyethylenated with 15 moles of ethylene oxide | 1.5 g |
| Pure cetyl alcohol | 1.5 g |
| Triethanolamine qs pH 5.5 | |
| Water | qs 100.0 g |

This milk, applied after permanent-waving enables ready disentangling of the wet hair and a good recovery of curl to be obtained after rinsing.

The dried hair is shiny, soft, smooth and lively.

We claim:

1. Cosmetic composition for the treatment and care of the hair, containing, in a cosmetically acceptable aqueous medium, in amounts sufficient to improve the appearance, feel or shape of the hair:

at least one cationic surfactant agent of formula (I):

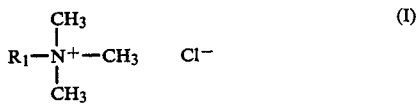

in which $R_1$ denotes a mixture of alkenyl and/or alkyl radicals having from 14 to 22 carbon atoms, derived from tallow fatty acids;

at least one quaternized hydroxyalkylcellulose polymer; and at least one ethoxylated copolymer of dimethylsiloxane/3-hydroxypropylmethylsiloxane.

2. Composition according to claim 1, wherein the quaternized hydroxyalkylcellulose polymer is chosen from:

quaternary derivatives of cellulose ether;

copolymers of cellulose or cellulose derivatives grafted with a water-soluble quaternary ammonium monomer.

3. Composition according to claim 2, wherein (1) the quaternary derivative of cellulose ether corresponds to the formula:

where $R_{Cell}$ is the residue of an anhydroglucose unit, y is a number equal to approximately 50 to approximately 20,000, and each $R_2$ individually denotes a substituent which is a group of general formula:

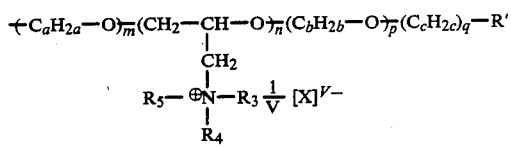

where a is an integer equal to 2 or 3;
b is an integer equal to 2 or 3;
c is an integer equal to 1 to 3;
m is an integer equal to 0 to 10;
n is an integer equal to 0 to 3;
p is an integer equal to 0 to 10;
q is an integer equal to 0 or 1;
R' is a hydrogen atom or a radical or formula:

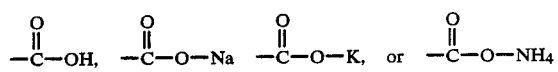

it being clearly understood that when q is equal to zero,

R' denotes —H;

$R_3$, $R_4$ and $R_5$, taken individually, each denote an alkyl, aryl, aralkyl, alkylaryl, cycloalkyl, alkoxyalkyl or alkoxyaryl radical, it being possible for each of the radicals $R_3$, $R_4$ and $R_5$ to contain up to 10 carbon atoms, it being clearly understood that, in the case of an alkoxyalkyl radical, there are at least 2 carbon atoms separating the oxygen atom from the nitrogen atom, and it also being clearly understood that the total number of carbon atoms present in the radicals denoted by $R_3$, $R_4$ and $R_5$ is between 3 and 12;

$R_3$, $R_4$ and $R_5$, taken together, can denote, with the nitrogen atom to which they are attached, one of the following radicals: pyridine, α-methylpyridine, 3,5-dimethylpyridine, 2,5-dimethylpryridine, 2,4,6-trimethylpyridine, N-methylpiperidine, N-ethylpiperidine, N-methylmorpholine or N-ethylmorpholine; X is an anion; V is an integer equal to the valency of X;

the average value of n per anhydroglucose unit in this cellulose ether is between 0.01 and approximately 1, and the average value of (m+n+p+q) per anhydroglucose unit in this cellulose ether is between approximately 0.01 and approximately 4;

(2) the copolymer of cellulose or cellulose derivative grafted with a water-soluble quaternary ammonium monomer is a graft copolymer of hydroxyalkylcellulose and a methacryloyltrimethylammonium salt, a methacrylamidopropyltrimethylammonium salt or a dimethyldiallylammonium salt.

4. Composition according to claim 1, containing 0.5 to 2.5% by weight, relative to the total weight of the composition, of the cationic surfactant agent of formula (I) defined in claim 1.

5. Composition according to claim 1, containing 0.5 to 2.5% by weight, relative to the total weight of the composition, of quaternized hydroxyalkylcellulose polymer.

6. Composition according to claim 1, which contains 0.4 to 3% by weight, relative to the total weight of the composition, of ethoxylated copolymer of dimethylsiloxane/3-hydroxypropylmethylsiloxane.

7. Composition according to claim 1, which is presented in the form of an aqueous solution, thickened or otherwise, a cream, a gel, an aerosol foam or a spray.

8. Composition according to claim 1, which contains perfumes, colourings, emulsifiers, thickeners, sequestering agents, emollients, other cationic surfactant agents or any other adjuvant customarily used in hair-care formulation.

9. Composition according to claim 8, wherein the thickener is chosen from sodium alginate or gum arabic, cellulose derivatives, guar gum or its derivatives, xanthan gum or scleroglucans, the concentration of which varies from 0.1 to 30% by weight relative to the total weight of the composition.

10. Composition according to claim 1, wherein the pH is between 3 and 10.

11. Cosmetic composition according to claim 1, which is packaged under pressure, in an aerosol device, to form a foam at the time of expulsion from the aerosol device.

12. Composition presented under pressure according to claim 11, which is packaged in the presence of a propellant gas present in proportions not exceeding 25% relative to the total weight of the composition, chosen from carbon dioxide, nitrogen, nitrous oxide, volatile hydrocarbons and nonhydrolisable fluorinated and/or chlorinated hydrocarbons.

13. Process for treatment of the hair, wherein a composition as defined in claim 1 is applied on the hair.

14. Process according to claim 13, wherein a composition as defined in claim 1 is applied in the form of a product to be rinsed before or after shampooing, before or afer dyeing or bleaching, before or after permanent-waving or straightening.

15. Cosmetic composition for the treatment and care of the hair comprising, in a cosmetically acceptable aqueous medium, by weight based on the total weight of the composition:

from 0.5 to 2.5% of at least one cationic surfactant agent having the formula $$R_1-\overset{\overset{\displaystyle CH_3}{|}}{\underset{\underset{\displaystyle CH_3}{|}}{N^+}}-CH_3 \quad Cl^- \quad (I)$$

in which $R_1$ denotes a mixture of alkenyl and/or alkyl radicals having from 14 to 22 carbon atoms, derived from tallow fatty acids;

from 0.5 to 2.5% by weight of at least one quaternized hydroxyalkylcellulose polymer; and from 0.4 to 3% of at least one ethoxylated copolymer of dimethylsiloxane/3-hydroxypropylmethylsiloxane.

* * * * *